United States Patent [19]

Karakelle et al.

[11] Patent Number: 4,844,986

[45] Date of Patent: Jul. 4, 1989

[54] METHOD FOR PREPARING LUBRICATED SURFACES AND PRODUCT

[75] Inventors: Mutlu Karakelle; Richard J. Zdrahala, both of Dayton, Ohio

[73] Assignee: Becton, Dickinson and Company, Franklin Lakes, N.J.

[21] Appl. No.: 155,904

[22] Filed: Feb. 16, 1988

[51] Int. Cl.$^4$ ................................................ B32B 9/04
[52] U.S. Cl. ........................................ 428/447; 427/2; 427/38; 427/40; 427/41; 427/387; 427/407.1; 427/412.1; 427/412.3; 427/412.4; 428/448
[58] Field of Search ............... 427/2, 38, 40, 41, 45.1, 427/387, 388.1, 389.7, 389.9, 393.5, 407.1, 407.2, 409, 412.1, 412.3, 412.4; 428/447, 448, 446

[56] References Cited

U.S. PATENT DOCUMENTS

| | | | |
|---|---|---|---|
| 3,847,652 | 11/1974 | Fletcher et al. | 427/41 |
| 4,072,769 | 2/1978 | Lidel | 427/38 |
| 4,177,301 | 12/1979 | Smith | 427/412.4 |
| 4,188,426 | 2/1980 | Auerbach | 427/40 |
| 4,210,696 | 7/1980 | Ikeda et al. | 427/412.1 |
| 4,292,397 | 9/1981 | Takeuchi et al. | 427/40 |
| 4,332,844 | 6/1982 | Hamada et al. | 427/412.1 |
| 4,344,981 | 8/1982 | Imada et al. | 427/40 |
| 4,445,991 | 5/1984 | Arbit | 204/168 |
| 4,477,517 | 10/1984 | Rummel | 427/387 |
| 4,533,369 | 8/1985 | Okita | 427/41 |
| 4,562,091 | 12/1985 | Sachdev et al. | 427/41 |
| 4,639,379 | 1/1987 | Asai et al. | 427/40 |
| 4,642,246 | 2/1987 | Janssen et al. | 427/127 |
| 4,720,521 | 1/1988 | Spielvogel et al. | 427/387 |

OTHER PUBLICATIONS

Rose et al., "Gas Plasma Technology and Surface Treatment of Polymers Prior to Adhesive Bonding", Plastics 85, pp. 685–688, 1985.

Inagaki et al., "Preparation of Siloxane-Like Films by Glow Discharge Polymerization", J. of Appl. Polymer Sci., vol. 29, pp. 3595–3605, 1984.

Primary Examiner—Sadie L. Childs
Attorney, Agent, or Firm—Richard E. Brown

[57] ABSTRACT

A method for preparing stable even coatings of a silicone lubricant on a low surface energy polymeric surface of an article includes plasma treatment of the surface in an atmosphere of a siloxane monomer. A layer of polysiloxane is deposited on the low energy surface to give a polysiloxane surface. A film of a polysiloxane lubricant having a surface tension substantially the same as or less than the surface energy of the polysiloxane surface is applied to the polysiloxane layer.

20 Claims, No Drawings

METHOD FOR PREPARING LUBRICATED SURFACES AND PRODUCT

BACKGROUND OF THE INVENTION

1. Field of the Invention.

This invention relates to lubrication of surfaces. More particularly, the invention relates to a method for lubricating a hydrophobic polymeric surface to give an even coat of lubricant which is stable over a protracted period.

2. Background of the Invention.

Many articles, devices and products require lubrication of a surface. In the medical instrumentation and diagnostic field, simple sensing devices such as, for example, thermometers, needles or electrode components of complex monitoring apparatuses must be inserted into a body cavity or through the skin and at a later time withdrawn. Absent effective lubrication which is stable throughout both the insertion and withdrawal stages of the procedure, severe patient discomfort may result.

Other medical articles, such as syringes, cannulas and catheters used for sampling or medicament administration, or devices such as burets used in diagnostic procedures, have components which are in sliding contact during use. Such devices require lubrication of the moving parts and may well also require lubrication of an external surface.

In the medical arts, synthetic polymers have come to the fore as materials of choice for fabrication of articles. Although polymers have many salubrious properties which make them useful in medical articles or devices, such as flexibility and biocompatibility consequent to chemical inertness, they have the disadvantage of being materials of low surface energy. One of the otherwise most useful classes of polymers, the perfluorinated hydrocarbons, has the lowest surface energy of any known polymer class.

Lubrication of surfaces of low surface energy is a long-standing problem because of the propensity of lubricants to migrate from surface to surface interfaces or to "bead" on an external surface. Either phenomenon severely limits the effectiveness of a lubricant on a low-energy surface.

Migration and beading of a lubricant on a surface are believed to be related to the surface tension of both the lubricant and the surface, and are easily understood with a simple and familiar analogy. Anyone who has ever washed and polished a car has observed water to form discreet drops on the hood after polishing. The same situation may exist when a lubricating oil is applied to a surface of an article. If the lubricant forms beads on the surface or migrates from a surface to surface interface, very ineffective lubrication results.

The antithesis of beading, i.e., the ability of a liquid to spread out and cover a surface is termed wettability and this property is measured by the conventional contact angle formed between the surface and a drop of the liquid applied to the surface. A high contact angle is indicative of beading. Conversely, a low contact angle indicates the desired spreading or wetting of the liquid. Complete spreading giving a uniform coating of the liquid on the surface is indicated by the theoretical contact angle of 0°.

Many attempts to achieve wetting of a surface with a liquid by addition of various surfactants have been reported. This approach has been partiallly successful with some surfaces, but no surfactant is known which allows formation of a uniform stable coating of a liquid on a perfluorinated surface. Other surface treatments which have been tried are strong acids, oxidizing agents and flame treatments.

Achievement of wettability to water by treatment of polymeric surfaces with an ionizing plasma formed by electromagnetic activation of a gas by either glow discharge or corona discharge is well-known and is summarized by Rose et al. in Proceedings of the SPE 43rd Annual Technical Conference and Exhibition, 685 (1985). Specific examples of enhancement of water wettability by plasma treatment of a polymeric surface are U.S. Pat. No. 4,445,991 to Arbit and U.S. Pat. No. 4,344,981 to Imada et al. The latter patent discloses that plasma treatment of a silicone surface gives water affinity of short duration, but that plasma treatment followed by treatment with an aqueous solution of a surface active agent gives water affinity of long duration.

U.S. Pat. No. 4,072,269 to Lidel discloses treatment of a polymeric surface with a plasma from an activator gas and a reactive gas whereby surface wettability to water is increased, but wettability to an oil is decreased, thereby inhibiting penetration of the oil into the polymer.

Enhancement of ink receptivity rendering polymeric surfaces printable is achieved by plasma treatment in U.S. Pat. No. 4,292,397 to Takeuchi et al.

Auerbach, in U.S. Pat. No. 4,188,426, discloses plasma deposition of a fluorocarbon coating onto an organic or inorganic surface wherein the lubricity, hydrophobicity and coefficient of friction of the resulting fluorocarbon surface are equivalent to those provided by conventional fluorocarbon polymers.

U.S. Pat. No. 4,642,246 to Janssen et al. has recently disclosed an approach to overcoming the problem of loss of lubricant from a magnetic disk by heating a polymeric lubricant having a terminal functional group to covalently bond the lubricant to surface polymers of the disk.

Preparation of films deposited by glow discharge or plasma polymerization of organosilanes, organosilazanes or organosiloxanes onto various surfaces such as polymers, glass and the like is known. Representative examples of such procedures are given in U.S. Pat. No. 4,562,091 to Sachdev et al., U.S. Pat. No. 4,639,379 to Asai et al. and in Inagaki et al., Journal of Applied Polymer Science, 29, 3595 (1984).

Copending application Ser. No. 036,733, filed Apr. 10, 1987, and having a common assignee herewith, discloses plasma treatment of a surface and lubrication thereof in a method to overcome breakout.

In spite of the vast literature on lubrication, the problem of providing stable lubricated surfaces for articles fabricated from polymeric surfaces of low energy has not yet been solved. It is toward the solution of this long-standing problem that this invention is directed.

SUMMARY OF THE INVENTION

A low energy surface of an article is lubricated by exposing the surface to a plasma generated from an organic monomer whereby a layer of a polymer is deposited on the surface. The layer of polymer, which is not lubricious itself, is then lubricated by applying thereto a film of a silicone oil.

Low energy polymeric surfaces, such as polyethylene, polypropylene, or most preferably, a perfluorinated polymer, such as fluorinated ethylene propylene copolymer (FEP) or polytetrafluoroethylene (PTFE) are particularly suited to lubrication by the method of the invention.

The choice of lubricant depends on the polymer deposited on the low energy surface. Preferably, the lubricant has a surface tension substantially the same as, or lower, than the surface energy of the polymer layer. Most preferably, a polysiloxane lubricant is applied to a silicon-containing polymer deposited onto the low energy surface.

In accordance with the method of the invention, lubricating oils may be applied to the lowest surface energy polymers known, the perfluorinated hydrocarbon polymers exemplified by FEP and PTFE in uniform fully-spread coatings. The coatings exhibit no tendency to migrate or bead for protracted periods, i.e., they have been observed to be stable for periods of fifteen months or more. Because of the known biocompatibility of silicones, the method of the invention is particularly well-suited, but not limited, to biochemical articles such as needles, syringes, catheters and the like, and greatly extends the usefulness of low-energy polymers in the fabrication of such articles.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

The present invention overcomes the problems of beading and migration with respect to application of lubricating oils to a surface and provides a method to achieve even coatings of lubricants on materials of low surface energy. The lubricant coatings of the invention may be applied in a uniform thickness, may cover the entire surface of the article and are stable for protracted periods.

Any material which, when fabricated into a useful article, exhibits a surface of low energy may be lubricated by the method of the invention. Suitable materials, for example, may be metal, glass, ceramic, or preferably, polymers. Representative nonlimiting examples of polymers responsive to the method are polyolefins such as polyethylene, and polypropylene, polystyrene, polyurethane, polyvinyl chloride or copolymers thereof. Particularly preferred surfaces are the perfluorinated polymers, as exemplified by PTFE and FEP.

In the first step of the preferred method of the invention, a polymer is plasma-deposited on a low-energy surface of an article. Deposition of a polymer onto a surface by generating a plasma from an organic monomer in the presence of the surface is well-known and representative examples of this technique are the disclosures of Auerbach, Asai et al., Sachdev et al. and Inagaki et al. above.

Any polymer can be deposited which raises the surface energy of the low-energy surface up to or above the surface tension of the lubricating oil to be applied in the second step of the method. Since the preferred lubricating oils are the polysiloxanes, a surface of suitable surface energy may be obtained by plasma depositing a silicon-containing polymer. Suitable polymers for depositing thus are polysilanes, polysilazanes and most preferably polysiloxanes.

The polymer layer to be deposited on the low-energy surface is formed by plasma polymerization of the corresponding monomer. Suitable monomers are, for example, hexamethyldisilozane, hexamethyldisilazane, hexamethylcyclotrisiloxane, octamethylcyclotetrasiloxane, tetramethylsilane, trimethylvinylsilane, trimethyltriethyldisiloxane, or substituted derivatives thereof wherein the substituent may be a halogen atom such as a fluoro or chloro group, or any other group, such as a nitro group which does not substantially interfere with the polymerization.

The plasma polymerization of the monomer onto the low energy surface may be carried out by any known plasma generating technique. The term "plasma" is used generally to describe the state of ionized gas, and consists of positively charged molecules or atoms and negatively charged electrons. The plasma may be generated by combustion, flames, physical shock or preferably by electrical discharge, such as a corona or most preferably a glow discharge. Glow discharge is most preferred because it is a cold plasma which does not deform polymeric surfaces of low melting point as may occur when using plasma generated by heat, as coronas.

A typical plasma generator, as, for example, that described in U.S. Pat. No. 3,847,652, consists of a reaction chamber, a high frequency generator and matching network, high vacuum system, gas delivery system and temperature controllers.

A wide range of power settings, radio frequencies, durations of exposure, temperatures, monomer gas pressures and gas flow rates may be used for plasma generation. Desirable ranges for these parameters which provide advantageous results are: DC or AC power levels of up to 1000 watts; RF frequency of 0.05 to 50 megahertz, durations of 0.01 to 12 hours; temperatures of 0° to 200° C.; gas pressures of 0.1 to 100 torr; and gas flow rates of 1-200 cubic centimeters/min.

By appropriate selection of monomer and plasma parameters, uniform layers of polymer of from about 0.01 to 10 microns may be deposited on the low energy surface.

The thin layer of silicon-containing polymer thus deposited on the surface of the article is not lubricious and is not a lubricated surface satisfactory for fabrication of biomedical articles. Lubricity is introduced in the second step of the method of the invention by applying a thin film of a polysiloxane lubricant of surface tension substantially the same or less than the surface energy of the silicon-containing polymeric surface deposited in the first step.

The preferred lubricant is a silicone oil or mixture thereof having a molecular weight of from about 100 to 1,000,000, preferably from about 1,000 to 100,000.

The most preferred class of lubricants is the polydialkylsiloxanes of general structure I:

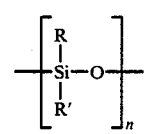

wherein each of R and R' may be independently a lower alkyl of 1 to 20 carbon atoms, preferably 1 to 8 carbon atoms, or may be joined into a silicon-containing ring of 5 to 8 carbon atoms, and n may be an integer from 1 to 2000, preferably 1 to 800. The preferred lubricants of structure I have viscosities of from about 10 to 1,000,000, preferably about 100 to 20,000 centistokes. The most preferred lubricant is DC-360$^R$ silicone oil of 12,500 centistokes (Dow Corning).

Application of a film of lubricant to the deposited polymeric surface may be accomplished by any suitable method, as, for example, dipping, brushing, spraying and the like. The lubricant may be applied neat or it may be applied in a solvent, and the solvent subsequently removed by evaporation. The lubricant film may be of any convenient thickness, and in practice, the thickness will be determined by such factors as the viscosity of the lubricant and the temperature of the application. For reasons of economy, the film preferably is applied as thinly as practical, since no significant advantage is gained by thicker films.

Catheters which are plasma treated and lubricated in accordance with Example I, below, and control catheters may be compared for stability of lubricant coatings by examination with an optical microscope. Penetration, insertion drag and retraction drag forces may be determined for the plasma treated and lubricated catheters and control catheters using an Instron Model 1122 tensile-testing apparatus as described in Example II, below.

The results of the wetting and force determinations are given in the Table, below.

forces as a result of the ten-fold increase in polymer layer thickness.

It is believed, although as yet not fully substantiated, that the plasma treatment induces cross-linking in the low energy surface and the deposited silicone polymer whereby both are converted to high molecular weight three dimensional polymer networks. It is further believed that highly reactive species, most likely free radicals, are formed in the deposited silicone polymer network and in the low energy surface which react together to provide a degree of chemical bonding. In addition to bonding, it is postulated that the plasma treatment induces portions of the polymer, most likely uncrosslinked ends, to enter openings generated in the low energy surface by the plasma treatment and ends of the lubricant chains to enter openings generated in the deposited polymer layer whereby the lubricant is substantially absorbed into the polymer layer and prevented from migrating or beading.

EXAMPLE I

Lubrication of Plasma Treated Catheters

The outside surfaces of FEP catheters (16 gauge) were plasma coated with layers of hexamethyldisilazane polymer 0.1$\mu$ and 1$\mu$ thick using a parallel plate plasma generating equipment at the following conditions: substrate temperature 82° C.; chamber pressure, 0.2 torr; frequency, 50 KHz; power, 125 watts; deposition time, 1 and 10 minutes; flow rate, 16cc/min. the coated cathe-

TABLE

| | Catheter | Catheter Lubricant | Lubricant Wetting | Average Penetration Force (Newtons) | Average Drag Force (Newtons) | |
|---|---|---|---|---|---|---|
| | | | | | Insertion | Retraction |
| 1 | Control FEP | None | — | 4.30 | 3.67 | 3.57 |
| 2 | Control FEP | DC 360 (12,500 cstks) Silicone fluid* | Random drops (beaded) | 1.61 | 0.42 | 0.76 |
| 3 | FEP, plasma treated, 0.1$\mu$ polymer coating | None | — | 4.92 | 2.78 | 1.57 |
| 4 | FEP, plasma treated, 0.1$\mu$ polymer coating | DC 360 (12,500 cstks) Silicone fluid* | Even wetting | 1.47 | 0.33 | 0.54 |
| 5 | FEP, plasma treated, 1.0$\mu$ polymer coating | None | — | 6.31 | 5.83 | 4.90 |
| 6 | FEP, plasma treated 1.0$\mu$ polymer coating | DC 360 (12,500 cstks) Silicone fluid | Even wetting | 1.39 | 0.34 | 0.60 |

*DC 360 (12,500 cstks) silicone fluid applied as 2 wt % solution in Freon TF$^R$.

It is seen by comparing catheter 2 with catheters 4 and 6 that the lubricant evenly wets the plasma treated catheters, but forms beads on the control catheter. The plasma treated catheters are still evenly wet after fifteen months.

Comparison of lubricated catheters 2,4 and 6 with unlubricated catheters 1,3 and 5 shows large reductions in the penetration and drag forces for the lubricated catheters. It is also seen from the data in the Table that plasma treated lubricated catheters 4 and 6 have lower forces than nonplasma treated lubricated catheter 2. The high penetration and drag forces observed for catheter 3 establish that lubricity is not introduced by the polymer layer but by the lubricant.

Comparison of the penetration and drag forces of catheters 4 and 6 reveals no appreciable change in the ters and control catheters were dipped into a 2% by weight solution of DC360$^R$/12,500 cstks (Dow Corning) silicone fluid in Freon TF$^R$ (DuPont) solution in order to apply silicone lubricant. The coating of silicone lubricant on the plasma treated catheters and the control catheters was examined periodically for fifteen months with an optical microscope. The lubricant on plasma-treated catheters remained even and fully spread, i.e., fully wetted, over this time period. The lubricant on the control catheters which were not plasma treated formed beads within a few minutes.

EXAMPLE II

Penetration and Drag Testing of Lubricated Catheters

The needle assembly of a 16 gauge tipped FEP catheter was attached to the upper jaw of the Instron Model 1122 tensile-testing equipment. A piece of 1/16 inch thick natural rubber (Type AA; B. F. Goodrich, Akron, Ohio) was attached at a 45° angle to the bottom of the Instron base. A new piece of natural rubber was used for testing each catheter. The upper jaw was lowered at a rate of 50 mm/min to achieve the penetration of the needle through the rubber membrane to the point where the hub of the catheter was about to touch the membrane. The jaw movement was then reversed at the same speed of 50 mm/min. Resisting forces exerted on the catheter were recorded during this process. The penetration, insertion drag and retraction drag forces were obtained from the recorded Instron force/time charts and are given in the Table.

Thus, the invention provides in its preferred embodiment, a method to lubricate a perfluorinated polymeric catheter so that the lubricant remains fully wetted for fifteen months or longer. In addition to being stable on the polymeric surface, the lubricant is highly effective, as attested by the penetration and drag forces, which are substantially reduced compared to nonplasma-treated control catheters.

What is claimed is:

1. A method for preparing a lubricated surface of an article comprising plasma depositing onto a polymeric surface a layer of a silicon-containing polymer to provide a silicon-containing polymeric surface and applying thereto a film of a polysiloxane lubricant, said film having a surface tension substantially the same as or less than the surface energy of said layer, said film thereby substantially fully wetting said layer.

2. The method in accordance with claim 1 wherein said polymeric surface onto which the siliconcontaining polymer is deposited is selected from the group of materials consisting of polyethylene, polypropylene, polyurethane, polystyrene, polyvinylchloride, polytetrafluoroethylene and fluorinated ethylene propylene copolymer.

3. The method in accordance with claim 1 wherein said silicon-containing polymer is selected from the group consisting of a polysiloxane, a polysilane and a polysilazane.

4. A method in accordance with claim 3 wherein said silicon-containing polymer is selected from the group consisting of polymers of hexamethyldisiloxane, hexamethyldisilazane, hexamethylcyclotrisiloxane, octamethylcyclotetrasiloxane, tetramethylsilane, trimethylvinylsilane and trimethyltriethyldisiloxane.

5. The method in accordance with claim 1 wherein said depositing step includes generating plasma by a radio frequency technique.

6. The method in accordance with claim 5 wherein said depositing step includes generating plasma at a radio frequency of about 0.05 to 50 megahertz.

7. The method in accordance with claim 1 wherein said depositing step includes generating plasma at a power of about 1 to 1000 watts.

8. The method in accordance with claim 1 wherein said depositing step includes generating plasma at a temperature of about 0° to 200° C.

9. The method in accordance with claim 1 wherein said depositing step includes generating plasma at a pressure of about 0.1 to 100 torr.

10. The method in accordance with claim 1 wherein said depositing step includes generating plasma at a gas flow rate of about 1 to 200 cubic centimeters per minute.

11. The method in accordance with claim 1 wherein said depositing step includes maintaining the plasma deposition for about 0.01 to 12 hours.

12. The method in accordance with claim 1 wherein said polysiloxane lubricant is a polydialkylsiloxane of the formula:

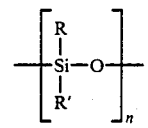

wherein R and R' are independently an alkyl group of 1 to 20 carbon atoms or are joined into a ring of 5 to 8 carbon atoms and n is an integer of from 1 to 2000.

13. The method in accordance with claim 12 wherein said polydialkylsiloxane is a polydimethylsiloxane.

14. The method in accordance with claim 12 wherein said lubricant has a viscosity from about 10 to 1,000,000 centistokes.

15. A method for preparing a lubricated surface of an article comprising plasma depositing onto a surface a layer of a polymeric substance to give a polymeric surface and applying thereto a film of a polysiloxane lubricant, said film having a surface tension substantially the same as or less than the surface energy of said layer, said film thereby substantially fully wetting said layer.

16. The method in accordance with claim 15 wherein said surface is selected from the group of materials consisting of a polymer, metal, glass and ceramic.

17. A method for preparing a lubricated perfluorinated polymeric surface of an article comprising:
   (a) subjecting a perfluorinated polymeric surface to an ionizing plasma generated by passing a radio frequency discharge through a siloxane whereby said siloxane is polymerized and deposited as a layer of polysiloxane on said perfluorinated polymeric surface to give a polysiloxane surface; and
   (b) applying to said polysiloxane surface a film of polysiloxane lubricant, said polysiloxane lubricant having a surface tension substantially the same as or less than the surface energy of said polysiloxane surface, said film thereby fully wetting said layer.

18. An article produced in accordance with the method of Claim 15.

19. The article of claim 18 being a medical device.

20. The article of claim 19 being a catheter.

* * * * *